United States Patent [19]

Hijikata et al.

[11] 4,308,822

[45] Jan. 5, 1982

[54] APPARATUS FOR APPLYING SAMPLE LIQUID ONTO SAMPLE BEARING FILM

[75] Inventors: Kazuo Hijikata; Ryo Fujimori, both of Hachioji, Japan

[73] Assignee: Olympus Optical Company Limited, Tokyo, Japan

[21] Appl. No.: 156,859

[22] Filed: Jun. 4, 1980

[30] Foreign Application Priority Data

Jun. 5, 1979 [JP] Japan .................. 54-69455

[51] Int. Cl.³ .................. B05C 1/16; B05C 11/00
[52] U.S. Cl. .................. 118/665; 118/681; 118/699; 118/713; 118/243
[58] Field of Search .............. 118/665, 712, 713, 703, 118/699, 668, 676, 680, 681, 243, 221

[56] References Cited

U.S. PATENT DOCUMENTS

| 3,289,581 | 12/1966 | Roozee | 118/712 X |
| 3,748,578 | 7/1973 | Ward | 118/712 X |
| 3,999,505 | 12/1976 | Kato et al. | 118/243 X |
| 4,173,943 | 11/1979 | Fujiwara et al. | 118/718 |
| 4,174,178 | 11/1979 | Ouchi et al. | 118/225 X |

FOREIGN PATENT DOCUMENTS 2821527  11/1978  Fed. Rep. of Germany .

Primary Examiner—John P. McIntosh

[57] ABSTRACT

An apparatus for applying a given amount of blood serum sample to a sample bearing film which has been wetted with Veronal-Veronal soda buffer solution comprises an applicator with an application chip holding a given amount of the blood serum sample, a hygrometer for detecting a humidity of an atmosphere surrounding the wetted sample bearing film, a timer circuit for presetting an application time in accordance with the detected humidity and producing a timing signal when said present application time has elapsed, and a control circuit for receiving the timing signal to drive the applicator to apply the blood serum sample to the film which is in the most favorable wet condition.

5 Claims, 4 Drawing Figures

APPARATUS FOR APPLYING SAMPLE LIQUID ONTO SAMPLE BEARING FILM

BACKGROUND OF THE INVENTION

This invention relates generally to an electrophoretic apparatus, and more particularly to an apparatus for applying a given amount of sample liquid such as blood serum sample onto a sampl bearing film which has been previously wetted with a buffer solution such as Veronal-Veronal soda solution.

In a known electrophoretic apparatus shown in FIG. 1 a sample bearing film 1 is wetted with a buffer solution 2 in a wetting section A by transporting the film 1 between a pair of rollers 3 made of sponge material, one of which is dipped in the buffer solution 2. Such a wetting section A is disclosed in U.S. Pat. No. 4,173,943. Then the wetted sample bearing film 1 is introduced in a sample applying section B which is isolated from an ambient atmosphere by a housing 4. In this section B are arranged a plurality of applicator chips 5 each of which holds at its front edge a given amount of sample liquid. Then the chips 5 are moved downward by means of a cam 6 and a motor 7 and are made in contact with the sample bearing film 1 to apply simultaneously a plurality of sample liquids onto the film 1. Usually a time duration from an instance when the sample bearing film 1 is wetted with the buffer solution 2 in the wetting section A to an instance at which the sample liquids are applied to the film 1, and a time period during which the applicator chips 5 are made in contact with the film 1 are fixedly predetermined to constant time periods. Therefore, even if the sample bearing film 1 has not a constant wet condition and thus, an absorbing ability of the film 1 varries due to a secular variation of the wet condition of the wetting rollers 3 and a variation of an ambient atmosphere, particularly humidity, the sample liquids are applied to the sample bearing film 1 always at a fixedly predetermined time instance. This results in that the sample liquids are not applied to the film 1 in a correct manner and thus, fractioned images might be affected seriously and accurate data could not be obtained. That is to say, when the sample bearing film 1 is too wetted, the sample liquids are liable to spread widely along the surface of film. In an extreme case adjacent samples might be contaminated with each other. When the film 1 is too dried, the sample liquids are not applied uniformly throughout the surface of film 1.

In the electrophoresis the wetness of the sample bearing film during the electrophoretic process is very important for obtaining accurately fractioned image. However, in the known electrohoretic apparatus the wetness of the sample bearing film under the electrophoretic process is not made constant.

SUMMARY OF THE INVENTION

The present invention has for its object to provide an apparatus for applying a given amount of sample liquid onto a wetted sample bearing film, which apparatus can overcome the above mentioned drawbacks of the known apparatus and can apply the sample liquid onto the film at such a timing that the film has a suitable wet condition for receiving the sample liquid in a desired manner.

It is another object of the invention to provide an apparatus for applying a given amount of sample liquid to a wetted sample bearing film, in which apparatus a timing of application of the sample liquid can be automatically preset in accordance with a wetness of the sample bearing film.

According to the invention an apparatus for applying a given amount of a sample liquid to a sample bearing film which has been previously wetted with a buffer solution comprises a sample applicator for holding the given amount of the sample liquid to be applied to the sample bearing film;

wetness detecting means for detecting a wetness of the sample bearing film wetted with the buffer solution;

a timer circuit for presetting, in accordance with the wetness detected by said wetness detecting means, an application time at which the sample liquid can be applied to the sample bearing film under such a condition that the film is in a suitable wet condition for being applied with the sample liquid; and a control circuit in response to a timing signal which is produced from said timer circuit when said preset application time has been elapsed, for actuating automatically said sample applicator to apply the sample liquid to the sample bearing film.

In a preferred embodiment of the apparatus according to the invention, said wetness detecting means produce an electrical amount representing the detected wetness of the sample bearing film, and said timer circuit has an input for receiving said electrical amount of the wetness detecting means and a circuit for automatically presetting said application time in response to said electrical amount.

In a further preferred embodiment of the apparatus according to the invention, said wetness detecting means comprise a meter for indicating the detected wetness of the sample bearing film, and said timer circuit comprises a presetting device for manually presetting said application time in accordance with an indication on said meter.

DESCRIPTION OF THE PREFERRED EMBODIMENTS

Figure 1:
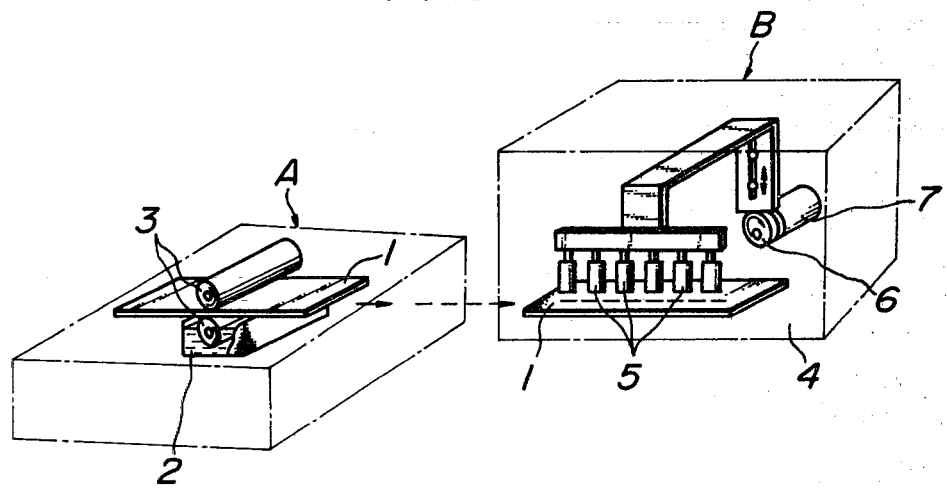
FIG. 1 is a perspective view showing schematically a known apparatus for applying sample liquids to a sample bearing film.
Figure 2:
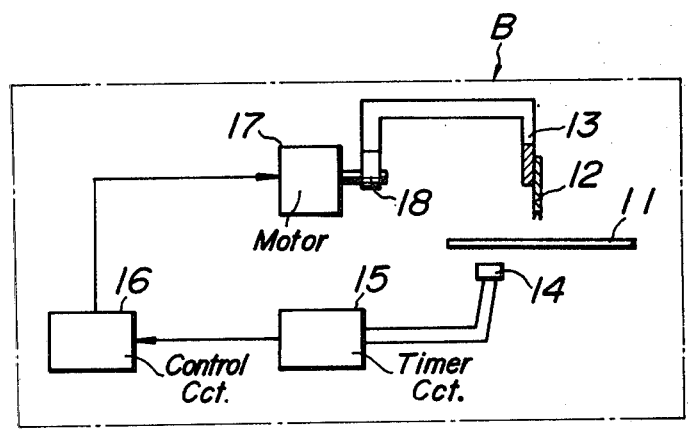
FIG. 2 is a schematic view illustrating an embodiment of a sample liquid applying apparatus according to the invention.

Referring to FIG. 2 a reference numeral 11 denotes a sample bearing film formed by a thin film of porous material such as cellulose acetate and a reference numeral 12 indicates one or more applicator chips secured to an applicator 13 which can move up and down. Near the film 11 is arranged a humidity sensor 14 for detecting a humidity of an atmosphere surrounding the film 11. The humidity sensor 14 may be of any desired type, and in this embodiment comprises a resistor whose resistance decreases upon an increase of humidity. The humidity sensor 14 is connected to a timer circuit 15 which produces a timing signal when a time period which is automatically preset in the timer circuit in accordance with a resistance value of the resistor in the humidity sensor 14 is elapsed. This preset time is so determined that the timing signal is produced when the wetted sample bearing film 11 has a suitable wet condition for being applied with the sample liquid held in the applicator chip 12. In this embodiment the humidity condition of the wetted film 11 is monitered indirectly from the humidity of the ambient atmosphere surrounding the film 11 as will be explained later with reference to FIG. 3. The timing signal thus produced from the timer circuit 15 is supplied to a control circuit 16 which then energizes a motor 17. A cam 18 is fixed to a driving shaft of the motor 18, with which cam 18 the applicator 13 is made in contact. Therefore the applicator 13 moves downward and the applicator chip 12 is brought into contact with the film 11 to apply the sample liquid onto the film 11.

Figure 3:
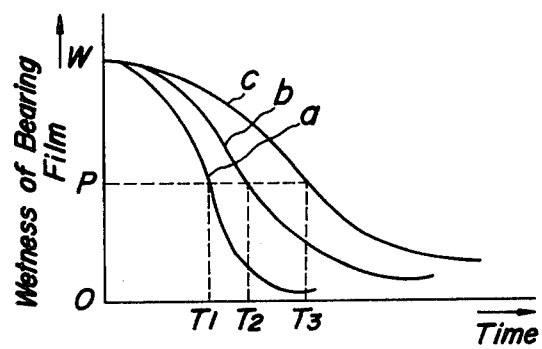
FIG. 3 is a graph showing variation of a wetness of a sample bearing film, when the wetted film is placed in the atmosphere.

FIG. 3 is a graph showing a variation of the wetness of the sample bearing film wetted with the buffer solution in accordance with a time. The measurement was effected under such a condition that the film is placed in the atmosphere having various humidities. A point W is a wetness of the film which has been just wetted with the buffer solution. A point P indicates an optimal wetness at which the sample liquid can be applied to the film in the most desirous manner. Curves a, b and c show a variation of wetness of the film under lower, middle and higher humidities, respectively of the atmosphere surrounding the film 11. As can be clearly understood from the graph, application times can be preset in the timer circuit 15 as $T_1$, $T_2$ and $T_3$ in FIG. 3 under the lower, middle and higher humidity conditions, respectively.

In the embodiment shown in FIG. 2, when the sufficiently wetted sample bearing film 11 is introduced into the applicating section B, the humidity sensor 14 detects a humidity of the atmosphere surrounding the film 11. Then the timer circuit 15 presets automatically an application time (for instance, the time $T_1$, $T_2$ or $T_3$ in FIG. 3) in dependence on the detected humidity. When this application time is elapsed, the timer circuit 15 produces a timing signal which is supplied to the control circuit 16. As soon as the control circuit 16 receives the timing signal from the timer circuit 15, the motor 17 is energized to move the applicator 13 downward to apply the sample liquid onto the sample bearing film 11 which is in the optimal wet condition. It should be noted that in order to avoid a vaporization of the sample liquid sticking on the applicator chip 12, it is preferable to stick the sample liquid onto the applicator chip 12 upon the generation of the application timing signal. In such a case the application time to be preset in the timer circuit 15 may be preferably shorter by a time period during which the sample liquid is stuck to the applicator chip 12. According to the invention the sample liquid can be automatically applied to the sample bearing film 11 which is in the most favorable wet condition of the sample application, even if a rate of variation in the wetness of the film might be changed due to various factors such as the humidity of the atmosphere surrounding the film. Further, since the sample bearing film 11 has a constant wetness at an end of the application of the sample liquid, the electrophoretic process can be initialed for the film of the constant wetness, even if a start timing of the electrophoretic process is fixedly predetermined. This feature offers an important advantage in designing the electrohoretic apparatus.

Figure 4:
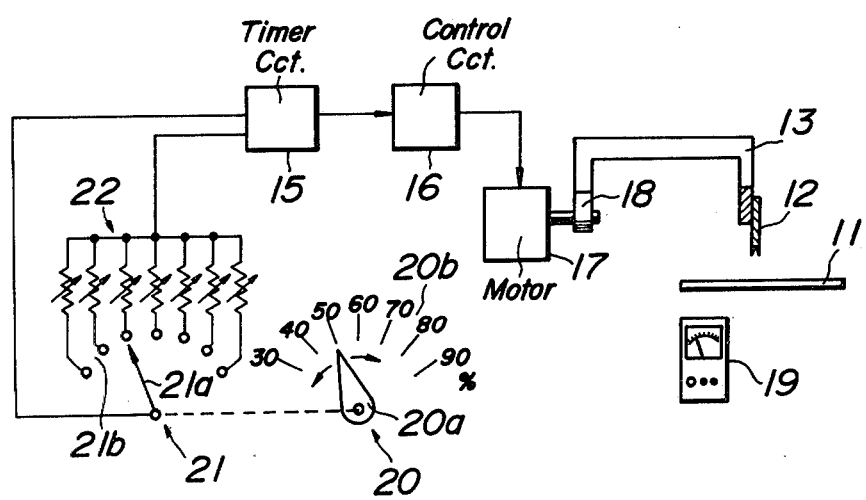
FIG. 4 is a schematic view showing another embodiment of the apparatus according to the invention.

FIG. 4 is a schematic view illustrating another embodiment of the apparatus according to the invention. In FIG. 4 the same portions as those shown in FIG. 2 are denoted by the same reference numerals and explanation about these portions is omitted. In this embodiment a hygrometer 19 is arranged near the sample bearing film 11. On a control panel is arranged a dial plate 20 having a plurality of humidity percentage values 20b. A knob 20a is rotatably arranged on the control panel. A rotating contact 21a of a rotary switch 21 is coaxially coupled with the knob 20a and a plurality of fixed contacts 21b of the rotary switch 21 are connected to respective variable resistors of a variable resistor group 22. These variable resistors have different values which gradually decrease in accordance with the increase of the humidity percentage values 20b on the dial plate 20.

In this embodiment an operator reads an indication of the humidity percentage value on the hygrometer 19 and sets this humidity value on the dial plate 20 by operating the knob 20a. Then, one of resistors of the variable resistor group 22 is selected in accordance with the detected humidity value. The timer circuit 15 comprises a RC time constant circuit to which said selected resistor is connected. Now the timer circuit 15 presets an application time determined by the resistance value of the selected variable resistor. When this application time has been elapsed, the timer circuit 15 generates a timing signal to actuate the control circuit 16 and just like as the previous embodiment the applicator chip 12 can be made in contact with the film 11 which is in the most favorable wet condition.

In the embodiment depicted in FIG. 4 the application timing can be preset in a discrete manner by means of the rotary switch 21 and the variable resistor group 22, but use may be made of a potentiometer having a slider arm which can be moved by an operating knob on the dial panel 20. In such a case the application timing can be preset in a continuous manner.

In the embodiments explained above, the applicator chip 12 is brought into contact with the wetted sample bearing film 11 at such a timing that the film has a favorable wet condition for being applied with the sample liquid. According to the invention, the applicator chip 12 may be made in contact with the sample bearing film 12 having a sufficiently wet condition and when the wetness of the film becomes the favorable condition, the applicator chip 12 may be removed from the film 11. In such a case the sample liquid stored in a recess formed in the front edge of blade-like applicator chip 12 as shown in the drawings could hardly spread over the surface of film 11 as long as the applicator chip 12 is made in contact with the film 11. Therefore it can be assumed that the sample liquid is applied to the film 11 when the applicator chip 12 is separated from the film 11.

As explained above, in the apparatus according to the invention the sample liquid such as blood serum can be automatically applied onto the sample bearing film which is wetted with the buffer solution such as Veronal-Veronal soda solution in the most favorable wet condition, although the wetness of the film might be changed due to various factors such as the humidity of the ambient atmosphere, amounts of buffer solution stuck to the applicator chip, and an absorbability of the sample bearing film. Therefore, the sample liquid can be applied to the sample bearing film in a highly uniform manner and the sharp fractioned image can be obtained. Further the electrophoretic process can be effected for the sample bearing film to which the sample liquid has been applied has a constant wetness and thus, the very accurate analysis can be carried out.

What is claimed is:

1. An apparatus for applying a given amount of a sample liquid to a sample bearing film which has been previously wetted with a sufficient amount of a buffer solution comprising: a sample applicator for holding the given amount of the sample liquid to be applied to the sample bearing film; wetness detecting means for metering a humidity of an atmosphere surrounding the sample bearing film wetted with the buffer solution to detect a wetness of the film; a variable timer circuit for presetting an application delay time as a function of the detected wetness of the film; a control circuit in response to a timing signal which is produced from said timer circuit when said preset application time has been elapsed, for actuating automatically said sample applicator to apply the sample liquid to the sample bearing film under such a condition that the film is in a suitable wet condition for being applied with the sample liquid.

2. An apparatus according to claim 1, wherein said wetness detecting means produce an electrical amount representing the detected wetness of the sample bearing film, and said timer circuit has an input for receiving said electrical amount of the wetness detecting means and a circuit for automatically presetting said application time in response to said electrical amount.

3. An apparatus according to claim 1, wherein said wetness detecting means comprise a meter for indicating the detected wetness of the sample bearing film, and said timer circuit comprises a presetting device for manually presetting said application time in accordance with an indication on said meter.

4. An apparatus according to claim 3, wherein said presetting device of the timer circuit comprises a rotary switch having a plurality of contacts each of which is connected to respective one of resistors having different resistance values, each of said resistors being connected in an RC time constant circuit for determining a given application time.

5. An apparatus according to claim 4, wherein each of said resistors is formed by a variable resistor.

* * * * *